(12) United States Patent
Wallon (10) Patent No.: US 11,761,949 B2
(45) Date of Patent: Sep. 19, 2023

(54) METHODS AND COMPOSITIONS FOR ASSESSING AND TREATING EMETOGENIC DRUG-RELATED NAUSEA

(71) Applicant: Lankenau Institute For Medical Research, Wynnewood, PA (US)

(72) Inventor: Margaretha Wallon, Ardmore, PA (US)

(73) Assignee: Lankenau Institute for Medical Research, Wynnewood, PA (US)

( * ) Notice: Subject to any disclaimer, the term of this patent is extended or adjusted under 35 U.S.C. 154(b) by 914 days.

(21) Appl. No.: 16/340,615

(22) PCT Filed: Oct. 9, 2017

(86) PCT No.: PCT/US2017/055730
§ 371 (c)(1),
(2) Date: Apr. 9, 2019

(87) PCT Pub. No.: WO2018/071323
PCT Pub. Date: Apr. 19, 2018

(65) Prior Publication Data
US 2019/0317114 A1  Oct. 17, 2019

Related U.S. Application Data (60) Provisional application No. 62/406,243, filed on Oct. 10, 2016.

(51) Int. Cl.
*G01N 33/49*    (2006.01)
*G01N 33/52*    (2006.01)
*G01N 33/80*    (2006.01)
*A61P 39/06*    (2006.01)
*A61P 1/08*     (2006.01)
*A61K 33/243*   (2019.01)
*G01N 33/53*    (2006.01)

(52) U.S. Cl.
CPC .......... *G01N 33/49* (2013.01); *A61K 33/243* (2019.01); *A61P 1/08* (2018.01); *A61P 39/06* (2018.01); *G01N 33/52* (2013.01); *G01N 33/5306* (2013.01); *G01N 33/80* (2013.01)

(58) Field of Classification Search
CPC .......... A61K 33/243; A61P 1/08; A61P 39/06; A61P 35/02; G01N 33/49; G01N 33/52; G01N 33/5306; G01N 33/80; G01N 33/50; G01N 33/5091
See application file for complete search history.

(56) References Cited

U.S. PATENT DOCUMENTS

| | | |
|---|---|---|
| 8,697,391 B2 | 4/2014 | Ayene |
| 9,186,357 B2 | 11/2015 | Trento et al. |
| 2010/0291057 A1 | 11/2010 | Kawaguchi |

OTHER PUBLICATIONS

Gura (Science, v278, 1997, pp. 1041-1042). (Year: 1997).*
Ji Johnson et al. Relationships between drug activity in NCI preclinical in vitro and in vivo models and early clinical trials. British Journal of Cancer, 2001, 9 sheets. (Year: 2001).*
Freshney. Culture of Animal Cells. A manual of basic technique. Alan R. Liss, 1983, New York, p. 4. (Year: 1983).*
Dermer (Bio/Technology, 1994, 12:320). (Year: 1994).*
Zheng et al. Journal of Hainan Medical University, 2017, published online Jul. 2016; 23(1): 72-75. (Year: 2016).*
Fleishman et al. Journal of Oncology Practice 8.3 (2012): 136-140. (Year: 2012).*
Tan et al. Journal of Experimental & Clinical Cancer Research 28.1 (2009): 1-7. (Year: 2009).*
Li et al. Toxicology in Vitro 27 (2013) 367-377 (Year: 2013).*
Kim et al. Journal of gynecologic oncology 23.2 (2012): 103-109 (Year: 2012).*
Osoba, D. et al. (Jan. 1997) Determinants of postchemotherapy nausea and vomiting in patients with cancer. Quality of Life and Symptom Control Committees of the National Cancer Institute of Canada Clinical Trials Group. J Clin Oncol 15, 116-123.
Bender, C. M., et al. (Mar./Apr. 2002) Chemotherapy-induced nausea and vomiting. Clin J Oncol Nurs 6, 94-102.
Chan, VT et al. Anti emetic therapy options for chemotherapy induced nausea and vomiting in breast cancer patients. Breast Cancer. 14 (Nov. 2011), vol. 3; pp. 151-160; p. 156, 2nd col. 2nd paragraph, p. 157, 2nd col., 1st paragraph; Table 2, DOI: 10.2147/BCTT.S12955.
Coskun, ZM et al. Evaluation of [Delta]"9-tetrahydrocannabinol metabolites and oxidative stress in type 2 diabetic rats. Iranian Journal of Basic Medical Sciences. (Feb. 2016), vol. 19, No. 2; pp. 154-158.
De Haes, J. C., et al. (Dec. 1990) Measuring psvchologicai and physical distress in cancer patients: structure and application of the Rotterdam Symptom Checklist. Br J Cancer 62, 1034-1038.
Grunberg, S. M., et al. (Apr. 2004) Incidence of chemotherapy-induced nausea and emesis after modem antiemetics. Cancer 100, 2261-2268.
Hesketh, P. J. (Jun. 2008) Chemotherapy-induced nausea and vomiting. N Engl J Med 358, 2482-2494.
Kutner, T. et. al., (Feb. 2017) "Preliminary evaluation of a predictive blood assay to identify patients at high risk for chemotherapy-induced nausa", Support Care Cancer, DOI 10.1007/s00520-016-3442-5, Springer-Verlag Berlin Heidelberg (Oct. 12, 2016 published online).
Li, J., et al. (Jan. 2014) A bioactive probe for glutathione-dependent antioxidant capacity in breast cancer patients: implications in measuring biological effects of arsenic compounds. J Pharmacol Toxicol Methods 69(1): 39-48; published online Oct. 20, 2013.
Molassiotis, A., et al. (May 2013) Development and preliminary validation of a risk prediction model for chemotherapy-related nausea and vomiting. Support Care Cancer 21, 2759-2767.

(Continued)

*Primary Examiner* — Mina Haghighatian
*Assistant Examiner* — Janice Y Silverman
(74) *Attorney, Agent, or Firm* — Howson & Howson LLP; Colleen M. Schaller (57) ABSTRACT

A method for assessing susceptibility to nausea of a patient comprises assessing the GSH recycling dependent antioxidant activity of the patient's blood cells prior to receiving an emetogenic agent, e.g., a cytostatic agent or a surgical anesthetic.

6 Claims, 1 Drawing Sheet

(56) References Cited

OTHER PUBLICATIONS

Raftos, J. E., et al. (May 2010) Glutathione synthesis and turnover in the human erythrocyte: alignment of a model based on detailed enzyme kinetics with experimental data. J Biol Chem 285, 23557-23567.

Roscoe, J. A., et al. (Jul. 2010) Insight in the prediction of chemotherapy-induced nausea. Support Care Cancer 18, 869-876.

Sekine. I., et al. (Mar. 2013) Risk factors of chemotherapy-induced nausea and vomiting: index for personalized antiemetic prophylaxis. Cancer Sci 104, 711-717.

Sun, C. C., et al. (Apr. 2005) Rankings and symptom assessments of side effects from chemotherapy: insights from experienced patients with ovarian cancer. Support Care Cancer 13, 219-227.

U.S. Department of Health and Human Sendees, N I H, National Cancer Institute. (Jun. 2010) Common Terminology Criteria for Adverse Events (CTCAE). version 4.03.

Verit, FF et al. Oxidative stress is associated with clinical severity of nausea and vomiting of pregnancy. American Journal of Perinatology. (Oct. 2007), Epub Sep. 24, 2007, vol. 24, No. 9; pp. 545-548.

Warr, D. G., et al. (Apr. 2005) Efficacy and tolerability of aprepitant for the prevention of chemotherapy-induced nausea and vomiting in patients with breast cancer after moderately emetogenic chemotherapy. J Clin Oncol 23, 2822-2830.

Yeo, W., et al. (Feb. 2009) A randomized study of aprepitant, ondansetron and dexamethasone for chemotherapy-induced nausea and vomiting in Chinese breast cancer patients receiving moderately emetogenic chemotherapy. Breast Cancer Res Treat 113, 529-535.

Wang, et al. Prospective feasibility study of a predictive blood assay to identify patients at high risk of chemotherapy-induced nausea. Journal of Clinical Oncology. May 20, 2016, vol. 34, No. 15_suppl; p. 6586, abstract. Published online May 11, 2017.

Jordan, et al. Guidelines for Antiemetic Treatment of Chemotherapy-Induced Nausea and Vomiting: Past, Present, and Future Recommendations. The Oncologist. Sep. 2007, vol. 12, No. 9, pp. 1143-1150.

Muchatuta, et al. Management of postoperative nausea and vomiting: focus on palonosetron. Ther Clin Risk Manag Feb. 2009;5(1):21-34. Epub Mar. 26, 2009.

International Search Report and Written Opinion, dated Feb. 20, 2018 in corresponding International Patent Application PCT/US17/055730, filed Oct. 9, 2017.

Rao KV, Faso A. Chemotherapy-induced nausea and vomiting: optimizing prevention and management. Am Health Drug Benefits. Jul. 2012;5(4):232-40.

\* cited by examiner

METHODS AND COMPOSITIONS FOR ASSESSING AND TREATING EMETOGENIC DRUG-RELATED NAUSEA

CROSS-REFERENCE TO RELATED APPLICATIONS

This application is a national stage of International Patent Application No. PCT/US2017/055730, filed Oct. 9, 2017, which claims the benefit of the priority of U.S. Provisional Patent Application No. 62/406,243, filed Oct. 10, 2016 (expired), which applications are incorporated herein by reference.

BACKGROUND OF THE INVENTION

Chemotherapy-induced nausea and vomiting (CINV) is a highly feared side effect in patients undergoing treatment for cancer.[15] CINV can negatively affect nutritional habits, ability to work and ability to follow recommended treatment regimens[1,2]. Today, virtually all chemotherapy agents are administered on an outpatient basis, enabled in large part by the development of effective antiemetic drugs.

While the development of antiemetic therapy has substantially reduced the incidence and severity of chemotherapy-associated vomiting, nausea has proven more difficult to assess and control since it is a subjective experience and therefore difficult to quantify. Even with modern interventions to prevent, manage and treat CINV, some patients will still experience moderate to severe nausea. This dilemma is illustrated by studies where patients receiving effective antiemetic regimens reported more nausea than vomiting[7]. In contrast to vomiting, nausea mechanisms are poorly understood, although it is widely thought that nausea reflects low-level activation of the vomiting pathway.

Assessment of the risk of CINV is an essential component of care for cancer patients receiving chemotherapy. Multiple factors influence the risk of CINV, with the emetogenic potential of chemotherapy drugs and dosages being the primary considerations. It is generally assumed that the strongest patient-related factors are younger age and female gender[4]. However, reports in the literature have demonstrated that using these factors clinicians may underestimate the likelihood of CINV, especially for delayed CINV[5,6].

Similar problems exist with postoperative nausea and vomiting (PONV), generally any nausea, retching, or vomiting occurring during the first 24-48 h after surgery. Reportedly, PONV occurs in 30% of post-surgical patients and up to 80% in high-risk patients. Nausea and vomiting is a common postoperative result that can increase inpatient costs and increase unplanned hospital admissions in outpatients.

Accurate prediction and adequate control of nausea remains a medical challenge. Risk assessment tools to avert the distress associated with CINV or PONV remain an unmet need in efforts to improve quality of life and treatment experience of patients[3].

SUMMARY OF THE INVENTION

The inventors have discovered a method for predicting the occurrence of a disposition to emetogenic agent/drug-related nausea in mammalian, i.e., human, subjects, by evaluating levels of oxidative stress in the subject's bloodstream prior to administration of the emetogenic agent. Thus, they have developed a novel use for assays directed to the detection of oxidative stress and toxicity in the blood, which permit an optimized treatment or drug regimen for the subject. The method relies on correlating oxidative stress indicators to nausea response.

In one aspect, a method for assessing susceptibility to nausea comprises assaying a biological sample containing red blood cells for a level of oxidative stress. The sample is obtained from a mammalian subject prior to administration of an emetogenic agent. In one embodiment, the assaying is performed by assessing the glutathione (GSH) recycling dependent antioxidant activity of the RBC in the sample as an indicator of oxidative stress.

In another aspect, the method for assessing susceptibility for nausea involves the above-described assaying step and further comprises optimizing the subject's treatment by treating the subject with a selected antiemetic drug regimen prior to, during, or after administration of the emetogenic agent, when the subject's RBCs demonstrate a certain level of glutathione recycling activity.

In another aspect, a method for treating a subject with cancer comprises assaying a biological sample containing RBC for a level of oxidative stress, the sample obtained from a mammalian subject prior to administration of an emetogenic cytostatic chemotherapeutic drug; determining the level of oxidative stress in the sample; and administering to the subject a therapeutic regimen. The therapeutic regimen is selected from various regimens involving emetogenic cytostatic agents with or without an antiemetic drug regimen. The various antiemetic drug regimens involves the administration of no antiemetic drugs, up to 2 antiemetic drugs, or 3 or more antiemetic drugs in association with the administration of the emetogenic agent. The selection of the therapeutic antiemetic drug regimen depends upon the level of oxidative stress in the sample.

In another aspect, a method of reducing the toxicity of drug regimens comprises assaying a biological sample containing RBC for a level of oxidative stress, the sample obtained from a mammalian subject prior to administration of an emetogenic agent; and reducing or eliminating the number of antiemetic drugs administered to the subject before, during or after administration of an emetogenic agent depending upon the level of oxidative stress.

In another aspect, a method of selecting a patient sample comprises providing at least one reagent capable of interacting with RBC and generating an indicator of oxidative stress in a blood sample of a patient obtained prior to treatment with an emetogenic agent; detecting in the sample from the patient the level of oxidative stress by providing a measurement of GSH recycling dependent antioxidant activity in the RBC; and classifying the sample of the patient from the outcome of the comparison in step (b) into one of at least two classifications of low or high oxidative stress levels to permit selection of a drug regimen.

In still another aspect, a method of managing a chemotherapeutic treatment in a subject having cancer involves determining whether the subject has a low oxidative level in a blood sample taken prior to administration of an emetogenic cytostatic chemotherapeutic agent; and managing a future therapeutic regimen for the subject based on the determining step.

In yet another aspect, a method of determining an individualized chemotherapeutic regimen for a human subject with cancer comprises performing an assay to evaluate the subject's blood sample's glutathione recycling dependent antioxidant activity and efficiency for scavenging free radicals prior to initiating an emetogenic agent and antiemetic drug regimen.

In a further aspect, a method of managing nausea in a surgical subject involves determining whether the subject has a low oxidative level in a blood sample taken prior to administration of an emetogenic anesthesia agent; and managing a future therapeutic regimen for the subject based on the determining step.

In still another aspect, a system for determining whether a subject has a high or low nausea response to an emetogenic agent, the system comprising: (a) assay reagents for measuring oxidative stress in the RBC of a whole blood sample taken from the subject prior to treatment with the emetogenic agent; and (b) a nausea phenotype determination element for determining whether the subject has a nausea resistant or a nausea predisposed phenotype.

Other aspects and advantages of these compositions and methods are described further in the following detailed description of the preferred embodiments thereof.

BRIEF DESCRIPTION OF THE DRAWINGS

FIG. 1 is a graph showing the stability of glutathione recycling activities in whole blood. Six randomly chosen patients were used to test the stability over time of the glutathione recycling pathways. Each sample was tested same day as it was drawn and then stored at 4° C. in between assays. Samples were tested at 24, 48 and 72 hours after blood draw and assayed as described in Example 1. Each data point represents the mean for each sampled assessed in quadruplicate.

DETAILED DESCRIPTION

Methods and compositions described herein are directed for use in assessing susceptibility to nausea in subjects prior to treatment or administration of emetogenic agents and using that assessment to create or modify therapeutic regimens involving co-administration of the emetogenic agent with a selected number of antiemetic drugs.

While not wishing to be bound by theory, nausea is mediated by drug-induced (e.g., chemotherapy-induced) free radicals in the small intestine, which trigger serotonin release from enterochromaffin cells in the gastrointestinal mucosa and activate 5-hydroxytryptamine3 (5-HT3) receptors, both in the chemoreceptor trigger zone in the bowel wall and in vagal afferent neurons[8]. The inventors hypothesized that a patient's risk of CINV or other emetogenic drug-induced nausea may reflect individual variations in the efficiency to scavenge free radicals after drug (e.g., chemotherapy) treatment. The inventors used as a marker for nausea the oxidation-reduction (redox) homeostasis as maintained by glutathione (GSH), a major antioxidant and free radical scavenger in the body[9,10]. GSH activity is known to be a critical determinant in the capability of cells to respond to bursts of free radicals generated by chemotherapy treatment[9]. Effective redox cycling of GSH is an important way in which cells detoxify reactive oxygen species to minimize tissue damage. The inventors identified a correlation between the oxidation-reduction (redox) homeostasis as maintained by glutathione (GSH), a major antioxidant and free radical scavenger in the body, particularly the oxidation-reduction (redox) homeostasis as maintained by glutathione (GSH), a major antioxidant and free radical scavenger, with nausea response in subjects.

In one aspect, a method for assessing susceptibility to nausea comprises assaying a mammalian subject's biological sample containing red blood cells (RBC) for a level of oxidative stress. Oxidative stress is essentially an imbalance between the production of free radicals and the ability of the body to counteract or detoxify their harmful effects through neutralization by antioxidants. In one embodiment, the assaying is performed by assessing the glutathione (GSH) recycling dependent antioxidant activity of the RBC in the sample as an indicator of oxidative stress. The inventors surprising discovered that low glutathione recycling capacity of a subject's RBC (i.e., high oxidative stress) can be used as a predictor of moderate or severe nausea following administration of an emetogenic agent that is known to cause vomiting and nausea, e.g., CINV.

According to the methods described herein, the biological sample is obtained from a mammalian subject prior to administration of an emetogenic agent. By "biological sample" or "sample" as referred to herein, is meant a biological fluid containing red blood cells. In one embodiment, the biological sample is whole blood. In another embodiment, the sample is another fluid containing RBCs. In one embodiment, the sample is diluted. In another embodiment, the sample is a concentrated sample.

By "mammalian subject", "patient" or "subject" as used herein means a mammalian animal, including a human, a veterinary or farm animal, a domestic animal or pet, and animals normally used for clinical research. More specifically, the subject of these methods and compositions is a human. In one embodiment, the subject has a cancer. In another embodiment, the subject is a preoperative patient intending to undergo surgery. Still other mammalian subjects intending to receive emetogenic agents are included in this definition.

By "emetogenic agent" as referred to herein is meant a drug or agent for administration to a mammalian subject that can typically cause severe, or moderate or mild symptoms of nausea. In one embodiment, the agent causes CINV. In another embodiment, the agent is a cytostatic and/or chemotherapeutic drug. In one embodiment, the cytostatic agent is a platinum drug. In one embodiment, the drug is a highly emetogenic agent such as a platinum drug on an anthracycline. In one embodiment, the agent is cisplatin. In another embodiment, the agent is Adriamycin. In another embodiment, the chemotherapeutic is moderately emetogenic, such as carboplatin or oxaliplatin. In another embodiment, the chemotherapeutic is mildly emetogenic, such as a taxane, such as Taxol and Taxotere. Still other cytostatic chemotherapeutics known to the art are emetogenic and may be useful in the methods described herein. See for example the chemotherapies described in U.S. Pat. No. 9,186,357, incorporated by reference herein.

In still another embodiment, the emetogenic agent is an emetogenic anesthetic agent useful for surgical procedures. In one embodiment, the emetogenic is a general anesthetic used either by the intravenous route or by inhalation that renders the subject unconscious and incapable of perceiving pain. In one embodiment, the anesthetic is a volatile anesthetic generally administered via inhalation, such as nitrous oxide, and various halogenated agents such as desflurane, halothane, isoflurane, and sevoflurane. In other embodiment, the anesthetic is administered intravenously, and can include, without limitation, ketamine, propofol, thiopental, etomidate, methohexital, fospropofol, and other known anesthetics.

As used herein the term "cancer" refers to or describes the physiological condition in mammals that is typically characterized by unregulated cell growth. In one embodiment, the term "cancer" means any cancer characterized by the presence of a solid tumor. In another embodiment, a cancer is a hematological cancer. When referred to herein, a cancer includes, without limitation, melanoma, breast cancer, brain cancer, colon/rectal cancer, lung cancer, ovarian cancer, adrenal cancer, anal cancer, bile duct cancer, bladder cancer, bone cancer, endometrial cancer, esophagus cancer, eye cancer, kidney cancer, laryngeal cancer, liver cancer, head and neck cancer, nasopharyngeal cancer, osteosarcoma, oral cancer, ovarian cancer, pancreatic cancer, prostate cancer, rhabdomyosarcoma, salivary gland cancer, stomach cancer, testicular cancer, thyroid cancer, vaginal cancer, lung cancer, and neuroendocrine cancer.

"Antiemetic drug" as discussed herein refers to the drugs known to reduce nausea and vomiting. Such drugs include, without limitation, 5-$HT_3$ receptor antagonists such as Ondansetron, Granisetron, Tropisetron, Dolasetron, and Palonosetron, or steroids such as dexamethasone, or $NK_1$ receptor antagonists such as Aprepitant or Rolapitant. Other antiemetics include scopolamine, meclizine, diphenhydramine, dronabinol, nabilone. Certain phenothiazines as antiemetic drugs include chlorpromazine, prochlorperazine and promethazine. Substituted benzamides that are useful include metoclopramide and trimethobenzamide. Still other antiemetic drugs are known such as those described in U.S. Pat. No. 9,186,357, incorporated by reference herein.

By "antiemetic drug regimen" as used in the methods described herein is generally meant either the combined or sequential administration of 1 or 2 different antiemetic drugs or the combined or sequential administration of 3 to 10 different antiemetic drugs. In the methods described herein, selection of the ≤2 drug regimen (which can include no antiemetic drugs) or selection of the ≥3 drug regimen depends upon the oxidative level of the blood sample. Where the subject demonstrates a low glutathione (GSH) recycling dependent antioxidant activity (i.e., high oxidative stress), a drug regimen can be altered to include greater numbers of antiemetic drugs in the regimen. Where the subject demonstrates a high glutathione (GSH) recycling dependent antioxidant activity (i.e., low oxidative stress), a drug regimen can be altered to include lesser numbers of antiemetic drugs in the regimen or even eliminate the antiemetic drug regimen earlier in treatment or dispense with it as unnecessary.

By "glutathione recycling dependent antioxidant activity" is meant how well RBC can convert the tripeptide GSH from an oxidized state to a reduced state and neutralize reactive oxygen species. GSH protects human cells from oxidative stress and reactive oxygen species by recycling with its oxidized isoform glutathione disulfide (GSSG). Suitable GSH recycling dependent antioxidant activity is measurable in the biological samples of these methods, in one embodiment, by the use of the OxPhos™ Cell Survival Kit, cat. no. KLD-02, Rockland Inc., which is described in more detail in Example 1 below. This assay uses hydroxyethyl disulfide (HEDS) as an indirect indictor of glutathione-dependent detoxification involving conversion of GSH→GSSG→GSH which releases ß-mercaptoethanol (ME). In one embodiment the method employs the measurement of GSH recycling activity by quantifying the amount of ß-mercaptoethanol (ME) released by the blood sample treated with the reagent and spectophotochemically measuring absorbance readings of ME; converting absorbance readings into ME concentrations; normalizing ME concentrations to total red blood cell count at the time of blood draw; and measuring the GSH recycling dependent antioxidant activity of intact erythrocyte cells in the sample. In the Ox-Phos™ assay, the pre-mixed dithiobisnitrobenzoic acid (DNTB)[13] reagents are used to spectrophotometrically determine the conversion of HEDS into ME and absorbance readings are converted into ME concentrations and normalized to total red blood cell count (RBC×$10^6$), as determined at the time of blood draw. In one embodiment, GSH dependent antioxidant activity was calculated using the conversion factor provided with the OxPhos™ assay protocol and normalized to the total red blood cell count. Using standard methods in the examples described below, the activity measure was calculated as a cut-off (mean+2×SD=cut-off value) for nausea-associated recycling capacity to be about 1.0. In one embodiment, the GSH assay is that described in U.S. Pat. No. 8,697,391, incorporated herein by reference. The GSH assay provides a measurement of the efficiency of enzymes in six separate pathways that ensure that GSH can be repeatedly converted from reduced-to-oxidized-states to reduce cell damage and release of nausea-triggering factors.

As used herein, the phrase, low glutathione (GSH) recycling dependent antioxidant activity in the biological sample (i.e., high oxidative stress) is used to indicate a predisposition to nausea and is measured as a GSH recycling dependent antioxidant activity score of ≤1.0. As used herein, the phrase, high glutathione recycling dependent antioxidant activity in the biological sample (i.e., low oxidative stress) is used to indicate a resistance to nausea and is measured as a GSH recycling dependent antioxidant activity score of >1.0.

The terms "a" or "an" refers to one or more. For example, "an expression cassette" is understood to represent one or more such cassettes. As such, the terms "a" (or "an"), "one or more," and "at least one" are used interchangeably herein.

As used herein, the term "about" means a variability of plus or minus 10% from the reference given, unless otherwise specified.

The words "comprise", "comprises", and "comprising" are to be interpreted inclusively rather than exclusively, i.e., to include other unspecified components or process steps. The words "consist", "consisting", and its variants, are to be interpreted exclusively, rather than inclusively, i.e., to exclude components or steps not specifically recited.

Technical and scientific terms used herein have the same meaning as commonly understood by one of ordinary skill in the art to which this invention belongs and by reference to published texts, which provide one skilled in the art with a general guide to many of the terms used in the present application. The definitions contained in this specification are provided for clarity in describing the components and compositions herein and are not intended to limit the claimed invention.

Thus in one aspect, a method of predicting or assessing the susceptibility of a subject to nausea comprises assaying a biological sample containing RBC for a level of oxidative stress, said sample obtained from a mammalian subject prior to administration of an emetogenic agent. The method may be performed to assess susceptibility to drug-induced nausea. In certain embodiments of the method, the drug is a cytostatic or chemotherapeutic agent or a general anesthetic agent.

In one embodiment as described above, the indicator of oxidative stress is GSH recycling capacity. According to the method, the subject's blood is obtained prior to treatment with the emetogenic agent. The sample, e.g., a sample of whole blood, is obtained from a mammalian subject prior to administration of a drug with an emetogenic reagent. The sample is contacted with assay components that permit an assessment of the oxidative potential of the RBC in the sample, such as the GSH recycling dependent antioxidant activity of the blood cells. In one embodiment, the blood is tested for GSH recycling activity immediately post-draw. In other embodiments, the blood is tested for GSH recycling activity after storage. It is anticipated the GSH recycling activity of the blood remains stable for hours to days following draw.

This method, in one embodiment, involves contacting the sample with HEDS and further comprise the steps above described for the GSH assay, i.e., quantifying the amount of ME released by the sample treated with the HEDS and spectrophotometrically measuring absorbance readings of ME; converting absorbance readings into ME concentrations; normalizing ME concentrations to total RBC count; and measuring the GSH recycling dependent antioxidant activity of intact RBC in said sample. These steps are performed to determine whether the subject's blood sample or biological sample is characterized as having a low or high glutathione (GSH) recycling dependent antioxidant activity. This method further permits diagnosing the subject as likely to experience emetogenic agent-related moderate to severe nausea when the sample indicates a low GSH recycling capacity.

In one specific embodiment, the method is applicable to a subject having a cancer requiring treatment with an emetogenic cytostatic agent. The cytostatic agent may be administered in any convenient method. In one embodiment, the nausea is chemotherapeutic induced nausea-vomiting (CINV). In one embodiment the cytostatic agent is administered intravenously. In another embodiment, the method of assessing susceptibility of a subject further comprises predicting delayed nausea for a subject with cancer during treatment with a highly or moderately emetogenic cytostatic chemotherapeutic drug.

In another embodiment, the method is applied to a subject, e.g., a pre-operative subject, undergoing a surgical procedure requiring an emetogenic general anesthesia agent. The anesthetic agent is administered intravenously or via inhalation. In another embodiment, the method further comprises predicting delayed nausea for a subject with undergoing surgery requiring an emetogenic general anesthetic agent.

In yet another aspect, the method for assessing susceptibility to nausea in a subject further comprises optimizing the subject's treatment by selecting and treating the subject with an antiemetic drug regimen prior to, during, or after administration of the emetogenic agent. In one embodiment, when the subject's RBCs demonstrate a low glutathione recycling capacity, the antiemetic drug regimen is altered to increase antiemetic reagents. This in one embodiment, the method involves further comprising optimizing the subject's treatment by treating the subject having cancer with an antiemetic drug regimen prior to, during, or after administration of a highly or moderately emetogenic chemotherapeutic drug, when the subject's RBCs demonstrate a low GSH recycling activity. In another embodiment, the method involves optimizing the subject's treatment by treating the subject having cancer with an antiemetic drug regimen prior to, during or after administration of a low or moderately emetogenic chemotherapeutic drug, when the subject's RBCs demonstrate a low GSH recycling activity. In still another embodiment, the method involves optimizing the subject's treatment by treating the subject having cancer with an antiemetic drug regimen containing two or less different antiemetic drugs prior to, during, administration of a moderately emetogenic or low emetogenic chemotherapeutic or by excluding treatment with an antiemetic drug, when the subject's RBCs demonstrate a high glutathione recycling capacity.

In yet another aspect, the method for assessing susceptibility to nausea in a subject further comprises optimizing the subject's treatment by treating the subject undergoing surgery with an antiemetic drug regimen prior to, during or after administration of a highly or moderately emetogenic anesthetic agent, when the subject's RBCs demonstrate a low GSH recycling activity. In one embodiment, this method involves optimizing the subject's treatment by treating the subject undergoing surgery with a regimen of 2 or less antiemetic drugs prior to, during, administration of a moderately emetogenic or low emetogenic anesthetic agent or by excluding treatment with an antiemetic drug, when the subject's RBCs demonstrate a high glutathione recycling capacity.

In yet a further aspect, the method involves optimizing the subject's treatment by prescribing an antiemetic drug regimen to the subject when the subject's GSH recycling activity is lower than a cut-off characterized as a mean+2× Standard deviation of about 1.0. In yet another embodiment, a subject with cancer having a GSH recycling value lower than 1.0 is more likely to develop moderate-to-severe nausea during the early phase of chemotherapeutic treatment regimen than a subject with cancer having a value higher than 1.0. Therefore a further aspect of the method is optimizing the subject's treatment by prescribing an antiemetic drug regimen comprising three or more different antiemetic drugs to the subject with highly emetogenic chemotherapy, when the subject's GSH recycling activity is lower than a cut-off characterized as a mean+2× Standard deviation of about 1.0.

In one embodiment, the method permits a prediction of delayed nausea for a subject with cancer receiving highly emetogenic chemotherapy. In still another aspect, the method involves optimizing the subject's treatment by prescribing an antiemetic drug regimen to the subject when the subject's GSH recycling activity is lower than a cut-off characterized as a mean+2× Standard deviation of about 1.0. In another embodiment, the method can predict that a subject with cancer having a GSH recycling value lower than 1.0 is more likely to develop moderate-to-severe nausea during the early phase of chemotherapeutic treatment regimen than a subject with cancer having a value higher than 1.0.

In another aspect, a method for treating a subject with cancer comprises contacting a sample of whole blood obtained from a mammalian subject prior to administration of a drug with reagents that permit an assessment of the GSH recycling dependent antioxidant activity of the blood cells. In another embodiment, the method involves administering a highly emetogenic chemotherapeutic to the subject having a blood sample characterized by a high GSH recycling dependent antioxidant activity with a drug regimen of two or less different antiemetic drugs. It is also possible that lower doses of an antiemetic drug may also be prescribed. In another embodiment, the method comprises administering a low or moderately emetogenic chemotherapeutic to the subject having a blood sample characterized by a low GSH recycling dependent antioxidant activity also with a suitable antiemetic drug regimen.

In still other embodiments, for subjects having a high or low GSH recycling dependent antioxidant activity the method involves co-administering an antiemetic drug regimen or less than 2, 2, 3 or greater than 3 different antiemetic drugs with a high, low or moderately emetogenic chemotherapeutic.

In still another aspect, a method of determining an individualized chemotherapeutic regimen for an individual human subject with cancer comprising performing an assay to evaluate the subject's blood sample's glutathione recycling dependent antioxidant activity and efficiency for scavenging free radicals prior to initiating chemotherapy.

As demonstrated in the examples below, the redox assay capable of measuring GSH recycling in the blood was used to compare a patient's intrinsic ability to recycle GSH, before receiving chemotherapy with their later susceptibility to CINV after receiving treatment. The examples focused on platinum-based therapies, because they are known to be moderate-to-high risk inducers of nausea and vomiting, as they are administered to treat lung and colorectal cancers[11]. However, this supporting data shown in the examples below is believed to be extendable to broader patient demographics. The examples describe preliminary results from showing that a reduced ability to recycle GSH in the blood provides an objective indicator of the development of delayed nausea, addressing ambiguity in the current subjective tools used to assess CINV.

In yet another aspect, a method for treating a subject with cancer comprises assaying a biological sample containing RBC for a level of oxidative stress, said sample obtained from a mammalian subject prior to administration of an emetogenic chemotherapeutic drug. The method further involves determining the level of oxidative stress in said sample; and administering to said subject a therapeutic regimen depending upon the level of oxidative stress in the sample. In performing this method, the assaying is performed by assessing the glutathione (GSH) recycling dependent antioxidant activity of the RBC in the sample as an indicator of oxidative stress. In one embodiment the therapeutic regimen comprises administering a highly or moderately emetogenic chemotherapeutic with an antiemetic drug regimen consisting of ≤2 or ≥3 different antiemetic drugs. In another embodiment, the regimen comprises administering a highly or moderately emetogenic chemotherapeutic with ≤2 or no antiemetic drugs. In another embodiment, the regimen comprises administering a low emetogenic chemotherapeutic with ≤2 or no antiemetic drugs. In still another embodiment, the regimen involves administering a low emetogenic chemotherapeutic with no antiemetic drug. In one embodiment, the regimen selected from among those above mentioned when the subject's RBCs demonstrate a low GSH recycling activity is generally ≥2 or 3 different antiemetic drugs. In yet a further embodiment, the regimen involves administering a full course of an antiemetic drug with any emetogenic chemotherapeutic drug when the subject's RBCs demonstrate a high GSH recycling dependent antioxidant activity.

In another aspect, a method of reducing the toxicity of drug regimens comprises assaying a biological sample containing RBC for a level of oxidative stress, said sample obtained from a mammalian subject prior to administration of an emetogenic agent; and reducing or eliminating the number of antiemetic drugs administered to the subject before, during or after administration of an emetogenic agent depending upon the level of oxidative stress. In one embodiment, the assaying is performed by contacting the sample with a reagent that permits an assessment of the glutathione (GSH) recycling dependent antioxidant activity of the RBC in the sample as an indicator of oxidative stress. In another embodiment of this method, the appropriate reduction or elimination of the antiemetic drug is selected, when the subject's RBCs demonstrate a low GSH recycling dependent antioxidant activity. In another embodiment of this method, the subject receiving the drug regimen is a subject with cancer, and the emetogenic agent is a cytostatic agent. In another embodiment, the subject is undergoing a surgical procedure requiring an emetogenic general anesthesia agent.

In another aspect, a method of selecting a patient sample comprises providing at least one reagent capable of interacting with RBC and generating an indicator of oxidative stress in a blood sample of a patient obtained prior to treatment with an emetogenic agent. Thereafter the method involves detecting in said sample from said patient the level of oxidative stress by providing a measurement of GSH recycling dependent antioxidant activity in the RBC. The GSH recycling dependent antioxidant activity of the sample of said patient is classified into one of at least two classifications of either low or high oxidative stress levels to permit selection of a drug regimen. The drug regimen comprises the administration of ≤2 different antiemetic drugs or no antiemetic drugs before, during or after administration of a high to moderately emetogenic cytostatic chemotherapeutic agent, where the subject has cancer and a high GSH recycling dependent antioxidant activity. The drug regimen can also consist of the administration of ≤2 different antiemetic drugs or no antiemetic drugs before, during or after administration of a low emetogenic cytostatic chemotherapeutic, where the subject has cancer and a high or low GSH recycling dependent antioxidant activity. Still another drug regimen includes administering ≥3 different antiemetic drugs when the subject has cancer and a low GSH recycling dependent antioxidant activity. In another embodiment, the drug regimen can also be adjusted similarly in the case in which the emetogenic drug is an anesthesia, wherein the subject is undergoing a surgical procedure requiring anesthetics, and where the subject has a high or low GSH recycling dependent antioxidant activity.

In yet another aspect, a method of managing a chemotherapeutic treatment in a subject having cancer, comprises: (a) determining whether said subject has a low oxidative level in a blood sample taken prior to administration of an emetogenic cytostatic chemotherapeutic agent; and (b) managing a future therapeutic regimen for said subject based on said determining step (a) as described above.

In yet a further aspect, a method of managing nausea in a surgical subject, said method comprising: (a) determining whether said subject has a low oxidative level in a blood sample taken prior to administration of an emetogenic anesthesia agent; and (b) managing a future therapeutic regimen for said subject based on said determining step (a).

In another aspect, a method of selecting a population for individualized therapeutic regimen comprising classifying a patient for the likelihood of developing nausea into a low likelihood or high likelihood category prior to selecting or administering a drug regimen comprising a high or moderately emetogenic agent with a full ≥3 different antiemetic drugs or administering less numbers of the antiemetic drugs.

To perform one or more of the methods described herein, a system for determining whether a subject has a high or low nausea response to an emetogenic agent comprises: (a) assay reagents for measuring oxidative stress in the RBC of a whole blood sample taken from the subject prior to treatment with the emetogenic agent; and (b) a nausea phenotype determination element for determining whether said subject has a nausea resistant or a nausea predisposed phenotype. The phenotype determination element can include a reference profile for an oxidative level of RBC, e.g., a GSH recycling dependent antioxidant activity. In one embodiment, the phenotype determination element is obtained from a sample from one of more patients with a nausea resistant phenotype (e.g., GSH recycling dependent antioxidant activity of >1.0) or nausea predisposed phenotype (e.g., GSH recycling dependent antioxidant activity of ≤1.0).

In still a further aspect, a method for recommending a modification to a drug regimen prior to treatment of a subject with an emetogenic cytostatic or anesthetic agent comprises the following steps. First, a subject is identified who is prescribed therapy with an emetogenic agent. Then a prescribed therapeutic dose of said agent is determined. The level of oxidative stress in the RBC of the subject is measured prior to receiving the emetogenic, using GSH recycling dependent antioxidant activity as an oxidative stress indicator. The subject is identified as nausea resistant to highly/moderate emetogenic therapy if the GSH recycling capacity is greater than a predetermined level, and as nausea predisposed to said therapy if the GSH recycling capacity is lower than the predetermined level. Additional the method involves, in one embodiment, recommending a modification to the drug regimen if the subject is identified as nausea predisposed, wherein the modification comprises a discontinuation of the emetogenic agent or a replacement of the emetogenic agent with a new regimen comprising co-administering an antiemetic drug regimen with the emetogenic agent. In another embodiment, the method involves recommending a modification to the drug regimen if the subject is identified as nausea resistant, wherein the modification comprises comprising administering the emetogenic agent with an antiemetic drug regimen of 1 or 2 drugs, or with no antiemetic drug.

The following examples disclose specific embodiments of the methods and compositions described herein. These examples should be construed to encompass any and all variations that become evident as a result of the teaching provided herein.

Example 1: Materials and Methods

Patient Cohort

The study was conducted at Lankenau Medical Center in a collaboration of the Cancer Center with the Lankenau Institute for Medical Research (LIMR). Patients newly diagnosed with lung or colorectal cancer and initiating chemotherapy participated in the study as approved by the local Institutional Review Board (IRB). Written and signed informed consent was obtained from all patients. Adults (>18 years old) of both sexes were permitted following the protocol. All patients were treated according to current medical standards. Where choices were available, the medical staff had exclusive authority in recommending therapy based on patient-related matters, such as stage of disease and/or possible co-morbidities. Exclusion criteria included any prior chemotherapy, radiation therapy given within three months, current use of glutathione-containing supplements, and inability to provide written consent.

Each patient donated a tube of blood (12 mg $K_2$EDTA) and filled out the Rotterdam Symptom Checklist (RSCL) prior to each cycle of therapy[12]. During the study, 12 patients progressed while on protocol. These patients were equally divided between the colon and lung cancer patients and had their therapy modified to non-platinum-based therapies. All patients continued on the study unless transferred to hospice.

Glutathione Recycling Capacity

Blood samples were kept on ice until transferred to the lab. Samples were stored up to 3 days at 4° C. A commercial kit was used to measure GSH recycling capacity (OxPhos™ Cell Survival Kit, cat. no. KLD-02, Rockland Inc.). This assay uses hydroxyethyl disulfide (HEDS) as an indirect indictor of glutathione-dependent detoxification involving conversion of GSH→GSSG→GSH which releases ß-mercaptoethanol (ME) as quantified with dithiobisnitrobenzoic acid (DNTB)[13]. Whole blood was gently mixed and aliquots were transferred to microcentrifuge tubes containing 10 µl of HEDS reagent. Samples were incubated for 2 hrs. with gentle rocking at ambient temperature followed by centrifugation to pellet cellular material. Final supernatants were transferred into new tubes with pre-mixed (DNTB) reagents to spectrophotometrically determine the conversion of HEDS into ME at 412 nm (Beckman Coulter DU® 730). Following the vendor instructions, absorbance readings were converted into ME concentrations and normalized to total red blood cell count (RBC×$10^6$), as determined at the time of blood draw using a Sysmex XN-1000 in the clinical lab.

Stability of Glutathione Recycling Capacity

The stability of the glutathione recycling metric as determined by the assay in whole blood was confirmed by replicating measurements of the same patient blood sample over four consecutive days after storage at 4° C., as described above. All blood samples were stored at 4° C. between sampling and were assayed in quadruplicate using the same kit during the entire time period.

Glutathione Recycling Capacity as Predictive Marker

As noted above; a modified version of the validated RSCL was used in the study[12]. A total of 27 health measures were listed and patients were asked to grade the severity of each side effect. Though our aim was to assess the ability of the glutathione recycling capacity assay to predict nausea, all 27 symptoms on the RSCL were included to minimize the risk of obtaining biased responses. Samples collected prior to commencing chemotherapy were used to predict nausea risk and the accompanying RSCL to determine patients' baseline level of nausea. Additional samples collected during therapy served to assess possible effect of chemotherapy on the recycling capacity and RSCLs were used to assess changes in nausea level.

No nausea was given a '0', while grade '1' indicated mild symptoms with no intervention. Moderate symptoms that indicated intervention were given grade '2', while severe, but not life-threatening symptoms were assigned grade '3', according to the CTCAE Adverse Events Guide of 2010[14]. Patients filled out the symptom list prior to each cycle and were asked to grade their health during the interval between treatment cycles.

Statistical Methods

SPSS package (version 8.0.3) was used for data analysis. Reported levels of nausea were analyzed against recycling capacity, age and sex. The latter two were included as they are frequently used to predict nausea. All assessments were performed using the two-sided Fisher's exact test with alpha <0.05.

Subject Accrual.

This study is currently being conducted at Lankenau Medical Center, a suburban healthcare center that treats cancers of all sites with breast, colon and lung being the three most frequent sites diagnosed yearly. In this first phase of the project, we focused on lung and colorectal cancers that constitute about 25% of the cancer patient population at this medical center. Patients were treated according to standard-of-care with cisplatin-based therapies (highly emetogenic chemotherapy[2]) and carboplatin or oxaliplatin-based therapies (moderately emetogenic chemotherapy MEC).

Glutathione recycling capacity among cancer patients receiving platinum-based therapy was assessed in 64 of the first 68 enrolled patients. The remaining four patients were not treated with a platinum-based therapy and therefore not included in the current assessment. All colorectal patients were given FOLFOX (leucovorin+fluorouracil [5-FU]+oxaliplatin) (N=34) (MEC), followed by Avastin and FOLFIRI (leucovorin+fluorouracil [5-FU]+Irinotecan) for those that progressed while receiving therapy (N=5). The lung cancer patients were treated with therapy regimen containing Carboplatin (N=25) (MEC), or Cisplatin (N=5) (HEC). Lung cancer patients typically received 4 cycles of therapy unless they progressed and were switched to palliative care. Colorectal cancer patients were treated for 12 cycles or, if they progressed, until they were taken off active treatment.

Patient Demographics.

The median age of participating patients was 63.4 years (range 24 to 91 years). Women represent 43.75% of the total cohort, and constitute 35.3% and 53.3% in the colorectal and lung cohorts, respectively. The female cohort was of similar median age and range (see Table I) and received predominantly MEC (89.3%). All patients receiving therapy classified as HEC were given cisplatin and independent of classification all patients received at least one other agent as part of their regimen. Antiemetic therapy was given to all patients prior to chemotherapy. The majority of patients (98.44%) received a 5-HT antagonist and/or corticosteroid treatment prior to chemotherapy. Twenty-two percent of patients also received a NK1 antagonist and of these 4 out of 5 were female. Most patients (64%) had also been given prescriptions for antiemetics to take at home prior to treatment consisting of a 5-HT antagonist. Of these patients, 64% were given the 5-HT antagonist in combination with prochlorperazine while 22% of patients were given 5-HT together with corticosteroid therapy. Only 18.8% of patients was given home antiemetics after chemotherapy. See Table I.

TABLE I

Patient Characteristics

| Characteristics | Patients (%) | No of Patients |
|---|---|---|
| Patients | — | 64 |
| Age (M ± SD) | 63.4 ± 12.8 | |
| Median age (range) | 64 (24-91) | |
| Total Female | 43.8 | 28 |
| Age (M ± SD) | 62.2 ± 13.1 | |
| Median age (range) | 64.5 (24-82) | |
| Primary Tumor | | |
| Colorectal | 53.1 | 34 |
| Lung | 46.9 | 30 |
| Chemotherapy Treatments | | |
| No. agents used per patient (M ± SD): 2.7 ± 0.70 | — | 64 |
| Patients receiving 3 or more chemotherapy agents | 54.7 | 35 |
| Highly emetogenic chemotherapy | 7.81 | 5 |
| Cis platin containing regimens | | |
| Moderately emetogenic chemotherapy | | |
| Carboplatin containing regimens | 39.06 | 35 |
| Oxaliplatin containing regimens | 53.12 | 34 |

TABLE I-continued

Patient Characteristics

| Characteristics | Patients (%) | No of Patients |
|---|---|---|
| Antiemetic Medication Characteristics | | |
| 5-HT Antagonists | 98.44 | 64 |
| Corticosteroids | 98.44 | 64 |
| NK1 Antagonist | 21.88 | — |
| No. of antiemetic agents used perpatient (M ± SD): 2.62 ± 0.70 | | |
| Patients receiving ≥2 antiemetic agents | 54.69 | 64 |
| Patients prescribed antiemetics at home prior to chemotherapy | 68.75 | 64 |
| Patients prescribed antiemetics at home post chemotherapy | 21.88 | 64 |

Incidence of Nausea.

Even with the administration of antiemetic therapy about 22% of cohort had moderate to severe nausea during the time between treatments (see Table II and III). The incidence was higher among the female subjects (29.6%, Table III); especially among the younger women (≤55 years of age, Table III) who were more than twice as likely (62.5%) to suffering delayed nausea compared to the overall cohort (see Table III). Among older women (≥56 years of age), nausea was no more frequent than in the overall cohort. Of those receiving cisplatin (HEC) (N=6) all were older and 4 were female. Only one female reported delayed nausea of the patients that reported nausea.

TABLE II

Patient Characteristics, Predicted and Reported Nausea

| Sex | Age | Recycling Capacity | Nausea Predicted | Nausea Reported |
|---|---|---|---|---|
| F | 60 | 0.81 | Yes | Yes |
| F | 75 | 0.98 | Yes | Yes |
| F | 67 | 0.61 | Yes | Yes |
| F | 51 | 0.85 | Yes | Yes |
| M | 72 | 0.73 | Yes | Yes |
| M | 47 | 0.96 | Yes | Yes |
| M | 65 | 0.92 | Yes | Yes |
| F | 49 | 0.86 | Yes | Yes |
| F | 46 | 0.79 | Yes | Yes |
| F | 62 | 0.95 | Yes | Yes |
| F | 43 | 3.16 | No | Yes |
| M | 29 | 3.1 | No | Yes |
| M | 34 | 3.2 | No | Yes |
| M | 62 | 1.7 | No | Yes |

TABLE III

Assay Characteristics.

| | No. | Nausea Incidence % | Sensitivity % | Specificity % | Correctly classified (%) |
|---|---|---|---|---|---|
| All | 64 | 21.9 | 69.2 | 96.0 | 89.1 |
| ≤55 years | 15 | 46.7 | 57.1 | 87.5 | 73.3 |
| ≥56 years | 49 | 14.3 | 71.4 | 95.2 | 91.8 |
| Female | 27 | 29.6 | 75.0 | 100.0 | 92.6 |
| ≤55 years | 8 | 62.5 | 60.0 | 100.0 | 75.0 |
| ≥56 years | 19 | 21.0 | 75.0 | 100.0 | 94.7 |

Stability of Glutathione Recycling Activities in Whole Blood.

Stability of thiol-containing factors in whole blood has been studied[10], however the stability of the assay readout as determined for recycling of GSH in whole blood[13] had not been established previously. Thus, we re-tested the same blood specimens from six individual subjects over four consecutive days to confirm stability in the readout metric. Recycling capacity was assessed as described above and results normalized to total red blood cell count, which was performed in the clinic on the day of blood draw. Mean values for glutathione-recycling activity over the four days are plotted with standard deviation (see FIG. 1). Standard deviation ranged from 0.04 (Pt. A) to 0.50 (Pt. D). In three specimens tested (Pt. A, B, C), the glutathione recycling capacity was stable after blood draw with <5% change up to 72 hrs. later. In the three other specimens (Pt. D, E, F), the glutathione capacity was stable during the first 24 hours but exhibited a ~20% reduction by 48 hours after blood draw. All tests were using the same OxPhos™ kit and the same scientist performed all the tests for all three subjects.

Glutathione Recycling Capacity as Predictor of Platinum-Based Delayed Nausea.

The tripeptide GSH protects human cells from oxidative stress and reactive oxygen species by recycling with its oxidized isoform glutathione disulfide (GSSG). Using the OxPhos™ kit we measured GSH recycling dependent antioxidant activity of intact erythrocyte cells in whole blood[13]. All blood samples were stored at 4° C. and analyzed in quadruplicate within 48 hr. GSH recycling capacity was calculated using the conversion factor provided with the assay protocol and normalized to the total red blood cell count.

Values obtained from the OxPhos™ test were compared to self-reported outcomes on the RSCL. With 56 patients available for analysis, we pooled all patients reporting no nausea ('not at all'; 0) with those reporting mild nausea ('a little'; 1), moderate ('quite a bit'; 2) or severe ('very much; 3). Patients with higher recycling capacity before onset of therapy reported no or mild nausea for the first four cycles of their treatment (see FIG. 2). On the other hand, those with low recycling capacity reported moderate to severe nausea. Using standard methods we calculated the cut-off (mean+ 2×SD=cut-off value) for nausea-associated recycling capacity to be 1.036. For practical purposes we used a cut-off 1.0 to predict nausea, so that patients with a value lower than 1.0 were deemed more likely to develop moderate-to-severe nausea during the early phase of their treatment regimen while those with values higher than 1.0 were predicted to experience no or mild nausea. After each patient finished their treatment, the test value prior to chemotherapy was compared to the RSCL responses for nausea. Through this approach, we correctly identified 89.1% of patients (p<0.0001). The overall sensitivity, low test score indicating risk of nausea, was 69.2% and specificity, high test score predicting low risk of nausea, was of 96.0% (see Table III).

Evaluating the test against other characteristics inducing therapeutic agent, the test performed better for patients receiving cisplatin- and carboplatin-based therapies than oxaliplatin (Table II). Two patient characteristics used to predict nausea and vomiting are age and gender. Patients 55 years of age or younger had higher incidence of nausea and were correctly identified in 46.7% (p 0.1818) of the cases. The female participants also experienced more nausea than the cohort in general, and the test correctly identified 92.6% of these subjects with 75% sensitivity and 100% specificity. Even though the number of female subjects younger than 56 was small, we correctly identified 75% (p 0.0014) of these subjects with similar sensitivity and specificity. Among subjects older than 56 years, whether in the general cohort or among female subjects only, we were able to correctly predict nausea for 91.8% and 94.7% of subjects, respectively.

Using patient characteristics such as female and young age (≤55 year) did not provide as accurate prediction with likelihood ratios of 1.504 (p 0.2325) and 2.778 (p 0.0314), respectively as did the recycling capacity assay (likelihood ratio 11.77, p<0.0001).

This is, to our knowledge, the first report demonstrating an unbiased method to predict delayed nausea for patients receiving chemotherapy. This new test could provide a low cost (e.g., ~$90) assessment of a patient's risk prior to initiating chemotherapy. Costly preventive agents, such as netupitant-palonosetron, can thereby be directed to patients likely to gain medical benefit from such agents, while generic, inexpensive agents will manage symptoms for others. Poorly controlled nausea could result in increased health care resources such as additional therapies or change in prophylaxis, but also affects the patients' work and social life in a negative way. If patients at high risk of nausea could be accurately identified, patient-oriented care might be markedly improved. Identification of high-risk patients could allow for a more appropriate preventive regimen and closer monitoring of these patients. Since antiemetics are not without toxicities themselves (such as insomnia, constipation or headaches), patients with low risk of nausea might be able to forego, or receive, dose-adjusted, antiemetics sparing them these toxicities and increasing cost-effectiveness of the care.

In this current study, as well as in other studies reported in the literature, about 20% of all cancer patients still suffer from nausea and vomiting (see Table III). In an effort to predict individual risk of CINV, clinicians can use patient characteristics or web-based prediction tools[16] and prediction indexes[17]. The sensitivity and specificity for either method is reported to range between 56%-75% depending on score results, resulting in 56%-74% of patients having a correctly classified risk of delayed CINV.

This study aimed to test if a new blood-based assay could improve the accuracy of the risk assessment for delayed nausea. The intent was to provide the medical field with an assay where patients could be tested prior to starting therapy, allowing for an optimal personalized preventive regimen.

Figure 1:
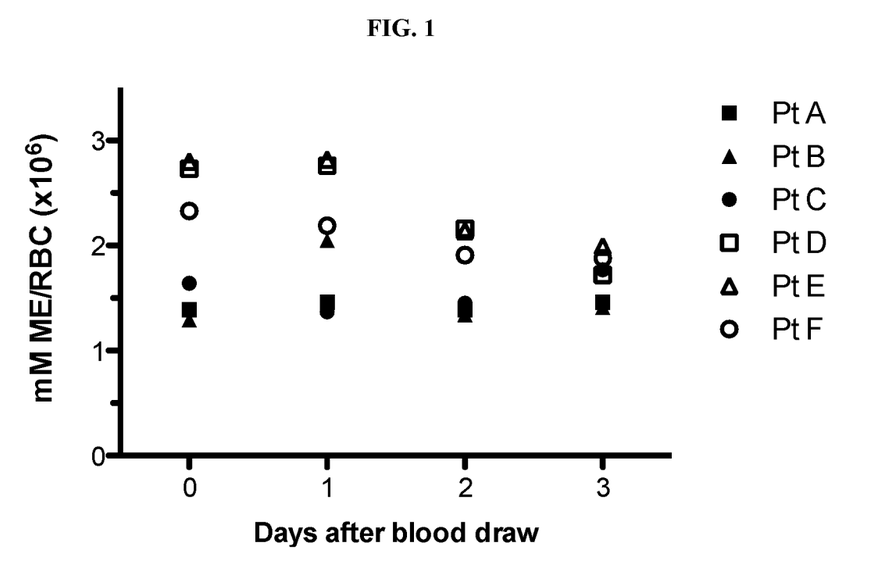

First, we wanted to ensure that the enzymes necessary for the recycling of glutathione were stable for at least 24 hours. As seen in FIG. 1, each sample was tested the day of blood collection and then stored at +4° C. and re-tested using the same kit for an additional 3 days. Test results after storage for 24 hours at +4° C. were essential identical to those obtained the same day of blood collection. After 48 hours at +4° C., half the samples generated stable results while the remaining samples produced results that were 80-85% of the original test result. This indicates that samples can be collected; stored, or shipped, overnight then tested the following day without any change in the precision of the risk assessment.

To evaluate the ability of this assay to predict delayed nausea we used blood drawn from chemotherapy naïve patients. All patients were treated at the Cancer Center of Lankenau Medical Center in Wynnewood, Pa., a suburb of Philadelphia, and with curative intent. Therefore, all colon and lung cancer patients were treated with fairly uniform regimens (see Table I). Test results were later compared to self-reported outcomes and medical charts. As seen in Table I, all patients received a platinum-based therapy with 98.44% of patients receiving identical preventive therapy for CINV. The preventive medication consisted of 5-HT antagonist (Palonosetron) and corticosteroid therapy (Dexamethasone) for essentially all patients. Some patients (21.88% of the cohort, 71% were females) also received a NK1 antagonist (Fosaprepitant) prior to chemotherapy. About two-thirds of patients had also received a similar regimen as premedication prior to the day of treatment.

Figure 2:
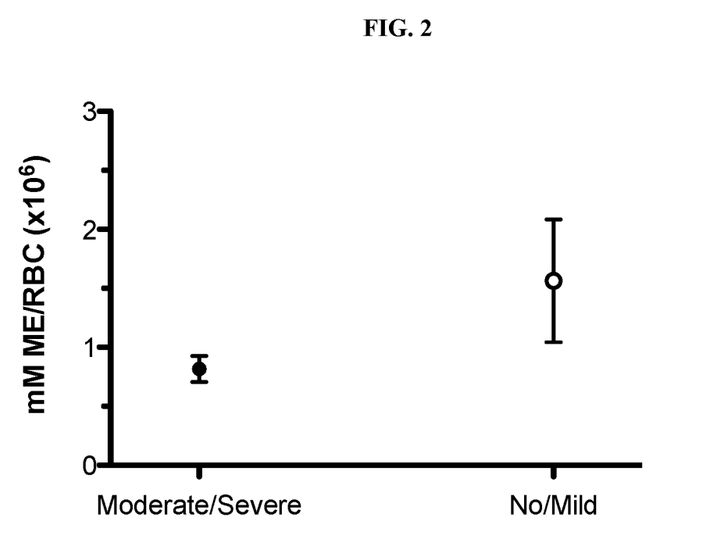
FIG. 2 is a graph showing that low glutathione recycling capacity is associated with moderate/severe nausea. Whole blood from patients receiving platinum-based therapy (N=64) for either lung or colorectal cancer was tested using the Oxo's™ kit. Results were then compared to the self-reported outcomes using a modified version of RSCL and the mean glutathione recycling capacity (mm ME/$10^6$ RBC) ±SD was plotted.

In this cohort, patients with low scores (<1.0) were more likely to report moderate or severe nausea during the interval period between the first four cycles than those with a score of 1 or higher (FIG. 2). Efficient recycling of glutathione, test score >1, could indicate more effective elimination of reactive oxygen species from the small intestines, resulting in diminishing release of signaling molecules that trigger nausea. Of concern is the number of patients where the test provided an incorrect prediction for nausea. In this study we identified 3 patients as having high risk (low test score) but never suffered any nausea and would have been overtreated if the test had been used to design preventive therapy. Likewise, we identified 4 patients as low risk (high test score) though they reported severe nausea during most of their regimen and even with several adjustments to their antiemetic prophylaxis (Table II). Three of four patients had unusually high test scores, exceeding 3, with no obvious explanation such as dietary supplementations that could affect glutathione levels or redox status. The same three patients had received a preventive regimen consisting of three classes of preventive agents and all were younger than 50 years of age. All others were correctly classified.

Though we tested blood samples from all treatment cycles, results from the sample collected prior to chemotherapy was not significantly different from samples collected at later cycles (data not shown). Therefore, we concluded that the recycling capacity is an individual characteristic and risk assessment can be performed on samples collected prior to chemotherapy and does not need to be repeated for later cycles.

Together, the results demonstrated that this assay could correctly classify 89.1% of patients with a sensitivity of 69.2% and 96.0% specificity. In accordance with the literature, we also found a higher incidence of nausea among younger patients than older (46.7% and 14.3%, respectively). Women were also more likely to suffer delayed nausea than the general cohort (29.6% versus 21.9%, respectively). Younger women reported higher incidence of nausea than the general younger cohort (62.5% versus 46.7%, respectively).

Among the patients receiving three agents as prophylaxis, 50% still suffered severe delayed nausea suggesting a need for new anti-nausea agents to be developed.

We anticipate that the results with a moderate cohort size (N=64) will be reproduced in larger populations of patients receiving other highly-emetogenic (anthracycline-based) and moderately-emetogenic (taxane-based) therapies.

The results of these assays conducted as described above on a cohort of patients are summarized in Table IV below.

TABLE IV

| | No. | Nausea Incidence % | Sensitivity % | Specificity % | Correctly classified (%) | Likelihood ratio |
|---|---|---|---|---|---|---|
| All | 56 | 19.6 | 66.7 | 90.9 | 85.7 | 7.33 |
| ≤55 yrs | 15 | 46.7 | 57.1 | 87.5 | 73.3 | nd |
| ≥56 yrs | 41 | 12.5 | 80.0 | 91.6 | 90.2 | nd |
| Female | 27 | 25.9 | 71.0 | 95.0 | 89.0 | 14.28 |
| ≤55 yrs | 9 | 44.4 | 75.0 | 100.0 | 89.0 | nd |
| ≥56 yrs | 18 | 16.7 | 93.0 | 100.0 | 94.0 | nd |

Specific Embodiments of the Invention

Certain embodiments of the invention are described as follows. It is understood that various steps and features of the method may be combined. Further as discussed above, in all of the below embodiments, a high level of oxidative stress (as defined in the specification above) is predictive of increased susceptibility to nausea. In circumstances where a subject demonstrates high oxidative stress (low GSH recycling activity), that subject's drug regimen can be designed to employ less emetogenic drugs to treat the disease or the addition of more anti-emetic drugs. In circumstances where a subject demonstrates low oxidative stress (high GSH recycling activity), that subject's drug regimen can be designed to employ higher emetogenic drugs or dosages to treat the disease (if more efficient or effective than the lower emetogenic drugs), with the addition of anti-emetic drugs. Alternatively, the subject with high GSH recycling activity (low oxidative stress) can receive lower emetogenic drugs for the disease with no or reduced anti-emetic drugs, to lower the toxicity or side effects of the anti-emetic drugs. Knowledge of the oxidative stress levels of the subject permits adjustment of disease treatment with the goal of greater comfort for the subject.

Thus, one embodiment is a method for assessing susceptibility to nausea that comprises assaying a biological sample containing RBC for a level of oxidative stress, said sample obtained from a mammalian subject prior to administration of an emetogenic agent. The sample is whole blood or another biological sample containing red blood cells (RBC).

In one embodiment, the assaying is performed by assessing the glutathione (GSH) recycling dependent antioxidant activity of the RBC in the sample as an indicator of oxidative stress. In another embodiment, the method includes contacting the sample with hydroxyethyldisulfide (HEDS).

In another embodiment, the method further comprises quantifying the amount of ß-mercaptoethanol (ME) released by the sample treated with the HEDS and spectrophotometrically measuring absorbance readings of ME; converting absorbance readings into ME concentrations; normalizing ME concentrations to total RBC count at the time of blood draw; measuring the GSH recycling dependent antioxidant activity of intact RBC in said sample, and diagnosing the subject as likely to experience emetogenic agent-related moderate to severe nausea when the sample indicates a low GSH recycling capacity. In another embodiment of the method, a low GSH recycling capacity is less than a mean+ 2× Standard deviation of about 1.0.

Still other embodiments, include practicing the method on a subject having a cancer requiring treatment with an emetogenic cytostatic agent or on a subject undergoing a surgical procedure requiring an emetogenic general anesthesia agent. In certain embodiments, the general anesthesia is administered intravenously or via inhalation.

In certain embodiments, the nausea being treated is chemotherapeutic induced nausea-vomiting (CINV).

In other embodiments, the method further comprises predicting delayed nausea for a subject with cancer during treatment with a highly or moderately emetogenic cytostatic chemotherapeutic drug. In other embodiments, the method comprises predicting delayed nausea for a subject with undergoing surgery requiring an emetogenic general anesthetic agent. In still other embodiment, the subject's treatment is optimized by treating the subject with an antiemetic drug prior to, during, or after administration of said emetogenic agent, when the subject's RBCs demonstrate a low glutathione recycling capacity.

In still other embodiments, the method further comprises optimizing the subject's treatment by treating the subject having cancer with an antiemetic drug prior to, during, or after administration of a highly or moderately emetogenic chemotherapeutic drug, when the subject's RBCs demonstrate a low GSH recycling activity. In still other embodiments, the method further comprises optimizing the subject's treatment by treating the subject having cancer with a selected antiemetic drug regimen prior to, during or after administration of a low or moderately emetogenic chemotherapeutic drug, or eliminating the antiemetic regimen, when the subject's RBCs demonstrate a high GSH recycling activity.

In yet other embodiments, the method further comprises optimizing the subject's treatment by treating the subject having cancer when the subject's RBCs demonstrate a high glutathione recycling dependent antioxidant activity with an antiemetic drug regimen comprising 2 or less different antiemetic drugs prior to, during, administration of a moderately emetogenic or low emetogenic chemotherapeutic.

In another specific embodiment, the method further comprises optimizing the subject's treatment by treating the subject undergoing surgery with an antiemetic drug regimen comprising 3 or more different antiemetic drugs prior to, during or after administration of a highly or moderately emetogenic anesthetic agent, when the subject's RBCs demonstrate a low GSH recycling dependent antioxidant activity.

In another specific embodiment, the method further comprises optimizing the subject's treatment by treating the subject undergoing surgery with either an antiemetic drug regimen of 0, 1 or 2 different antiemetic drugs prior to, during, or after administration of a moderately emetogenic or low emetogenic anesthetic agent when the subject's RBCs demonstrate a high glutathione recycling dependent antioxidant activity.

In yet another embodiment, a method for treating a subject with cancer comprises:
  a. assaying a biological sample containing RBC for a level of oxidative stress, said sample obtained from a mammalian subject prior to administration of an emetogenic chemotherapeutic drug;
  b. determining the level of oxidative stress in said sample; and
  c. administering to said subject a selected therapeutic regimen depending upon the level of oxidative stress in the sample, wherein the regimen is selected from:
    i. a highly or moderately emetogenic chemotherapeutic with an antiemetic drug regimen of two or less antiemetic drugs;
    ii. a highly or moderately emetogenic chemotherapeutic with no antiemetic drug;
    iii. a low emetogenic chemotherapeutic with an antiemetic drug regimen of two or less antiemetic drugs;
    iv. a low emetogenic chemotherapeutic with no antiemetic drug; or
    v. a full regimen of at least 3 antiemetic drugs with any emetogenic chemotherapeutic drug.

In other embodiment, the method involves performing the assay by assessing the glutathione (GSH) recycling dependent antioxidant activity of the RBC in the sample as an indicator of oxidative stress.

In another embodiment, the method comprises selecting regimen (i) to (iv) when the subject's RBCs demonstrate a low GSH recycling dependent antioxidant activity.

In still another embodiment, a method of reducing the toxicity of drug regimens comprises
  a. assaying a biological sample containing RBC for a level of oxidative stress, said sample obtained from a mammalian subject prior to administration of an emetogenic agent; and
  b. reducing or eliminating the number of antiemetic drugs administered to the subject before, during or after administration of an emetogenic agent depending upon the level of oxidative stress.

In another embodiment, these methods comprise performing the assay by contacting the sample with a reagent that permits an assessment of the glutathione (GSH) recycling dependent antioxidant activity of the RBC in the sample as an indicator of oxidative stress.

In another embodiment, these methods comprise selecting the appropriate reduction or elimination of the number of antiemetic drugs in the drug regimen, when the subject's RBCs demonstrate a low GSH recycling dependent antioxidant activity.

In another embodiment, these methods involve the subject receiving the drug regimen being a subject with cancer, and the emetogenic agent being a cytostatic agent. In another embodiment, these methods involve treating the subject undergoing a surgical procedure requiring an emetogenic general anesthesia agent.

In another embodiment, a method of selecting a patient sample comprises
  (a) providing at least one reagent capable of interacting with red blood cells and generating an indicator of oxidative stress in a blood sample of a patient obtained prior to treatment with an emetogenic agent;
  (b) detecting in said sample from said patient the level of oxidative stress by providing a measurement of GSH recycling dependent antioxidant activity in the RBC;
  (c) classifying the sample of said patient from the outcome of the comparison in step (b) into one of at least two classifications of low or high oxidative stress levels to permit selection of a drug regimen, wherein the drug regimen comprises the administration of two or less than two antiemetic drugs, or no antiemetic drug or three or more antiemetic drugs, before, during or after administration of
    i. a high to moderately emetogenic cytostatic chemotherapeutic agent, where the subject has cancer;
    ii. a low emetogenic cytostatic chemotherapeutic, where the subject has cancer; or
    iii. an emetogenic anesthesia agent, wherein the subject is undergoing a surgical procedure.

In another embodiment, a method of managing a chemotherapeutic treatment in a subject having cancer comprises: (a) determining whether said subject has a low oxidative level in a blood sample taken prior to administration of an emetogenic cytostatic chemotherapeutic agent; and (b) managing a future therapeutic regimen for said subject based on said determining step (a).

In another embodiment, a method of managing nausea in a surgical subject, said method comprising: (a) determining whether said subject has a low oxidative level in a blood sample taken prior to administration of an emetogenic anesthesia agent; and (b) managing a future therapeutic regimen for said subject based on said determining step (a).

In another embodiment, a method of selecting a population for individualized therapeutic regimen comprising classifying a patient for the likelihood of developing nausea into a low likelihood or high likelihood category prior to selecting or administering a drug regimen comprising a high or moderately emetogenic agent with a two or less antiemetic drugs or greater than three antiemetic drugs.

In another embodiment, a system for determining whether a subject has a high or low nausea response to an emetogenic agent, said system comprising: (a) assay reagents for measuring oxidative stress in the RBC of a whole blood sample taken from the subject prior to treatment with the emetogenic agent; and (b) a nausea phenotype determination element for determining whether said subject has a is predisposed to nausea or resistant to nausea, the phenotype determination element comprising a reference profile for an oxidative level of RBC, wherein the phenotype determination element is obtained from a sample from one of more patients with a nausea predisposed phenotype or a nausea resistant phenotype.

In another embodiment, a method for recommending a modification to a drug regimen prior to treatment of a subject with an emetogenic cytostatic or anesthetic agent, the method comprises:

(a) identifying a subject who is prescribed therapy with an emetogenic agent;

(b) determining a prescribed drug regimen consisting of the emetogenic agent and multiple antiemetic drugs;

(c) measuring the level of oxidative stress in the RBC of the subject prior to receiving the emetogenic agent, using glutathione (GSH) recycling dependent antioxidant activity as an oxidative stress indicator;

(d) identifying the subject as nausea predisposed when administered highly/moderate emetogenic therapy if the GSH recycling activity is less than a predetermined level, and as nausea resistant to said therapy if the GSH recycling activity is greater than the predetermined level; and either
  i. recommending a modification to the drug regimen if the subject is identified as nausea predisposed, wherein the modification comprises a discontinuation of the emetogenic agent or a replacement of the emetogenic agent with a new regimen comprising co-administering three or more antiemetic drugs with the emetogenic agent; or
  ii. recommending a modification to the drug regimen if the subject is identified as nausea resistant, wherein the modification comprises comprising administering the emetogenic agent with a reduction in the number of antiemetic drugs or with no antiemetic drug.

Each and every patent, patent application, and publication, including websites cited throughout the specification, including priority U.S. Provisional Patent Application No. 62/406,243, filed Oct. 10, 2016, is incorporated herein by reference. While the invention has been described with reference to particular embodiments, it will be appreciated that modifications can be made without departing from the spirit of the invention. Such modifications are intended to fall within the scope of the appended claims.

REFERENCES

1. Osoba, D. et al. (1997) Determinants of postchemotherapy nausea and vomiting in patients with cancer. Quality of Life and Symptom Control Committees of the National Cancer Institute of Canada Clinical Trials Group. J Clin Oncol 15, 116-123
2. Roscoe, J. A., et al. (2010) Insight in the prediction of chemotherapy-induced nausea. Support Care Cancer 18, 869-876
3. Bender, C. M., et al. (2002) Chemotherapy-induced nausea and vomiting. Clin J Oncol Nurs 6, 94-102
4. Sekine, I., et al. (2013) Risk factors of chemotherapy-induced nausea and vomiting: index for personalized antiemetic prophylaxis. Cancer Sci 104, 711-717
5. Warr, D. G., et al. (2005) Efficacy and tolerability of aprepitant for the prevention of chemotherapy-induced nausea and vomiting in patients with breast cancer after moderately emetogenic chemotherapy. J Clin Oncol 23, 2822-2830
6. Yeo, W., et al. (2009) A randomized study of aprepitant, ondansetron and dexamethasone for chemotherapy-induced nausea and vomiting in Chinese breast cancer patients receiving moderately emetogenic chemotherapy. Breast Cancer Res Treat 113, 529-535
7. Grunberg, S. M., et al. (2004) Incidence of chemotherapy-induced nausea and emesis after modern antiemetics. Cancer 100, 2261-2268
8. Hesketh, P. J. (2008) Chemotherapy-induced nausea and vomiting. N Engl J Med 358, 2482-2494
9. Kolli, V. K., et al. (2007) Alteration in antioxidant defense mechanisms in the small intestines of methotrexate treated rats may contribute to its gastrointestinal toxicity. Cancer Therapy 5, 501-510
10. Raftos, J. E., et al. (2010) Glutathione synthesis and turnover in the human erythrocyte: alignment of a model based on detailed enzyme kinetics with experimental data. J Biol Chem 285, 23557-23567
11. Rugo, H. S. (2014) Management of chemotherapy-induced nausea and vomiting in clinical practice. Clin Adv Hematol Oncol 12 Suppl 9, 9-11
12. de Haes, J. C., et al. (1990) Measuring psychological and physical distress in cancer patients: structure and application of the Rotterdam Symptom Checklist. Br J Cancer 62, 1034-1038
13. Li, J., et al. (2014) A bioactive probe for glutathione-dependent antioxidant capacity in breast cancer patients: implications in measuring biological effects of arsenic compounds. J Pharmacol Toxicol Methods 69, 39-48
14. U.S. Department of Health and Human Services, N I H, National Cancer Institute. (2010) Common Terminology Criteria for Adverse Events (CTCAE). version 4.03
15. Sun, C. C., et al. (2005) Rankings and symptom assessments of side effects from chemotherapy: insights from experienced patients with ovarian cancer. Support Care Cancer 13, 219-227
16. Molassiotis, A., et al. (2013) Development and preliminary validation of a risk prediction model for chemotherapy-related nausea and vomiting. Support Care Cancer 21, 2759-2767
17. Dranitsaris, G., et al. (2013) Prospective validation of a prediction tool for identifying patients at high risk for chemotherapy-induced nausea and vomiting. J Support Oncol 11, 14-21
18. U.S. Pat. No. 9,186,357
19. U.S. Pat. No. 8,697,391
20. Kutner, T. et. al, "Preliminary evaluation of a predictive blood assay to identify patients at high risk of chemotherapy-induced nausea", Support Care Cancer, DOI 10.1007/s00520-016-3442-5, Springer-Verlag Berlin Heidelberg (12 Oct. 2016 published on-line).

The invention claimed is:

1. A method for managing emetogenic drug-induced nausea in a mammalian subject with cancer, the method comprising:
  a. assaying a biological sample containing red blood cells (RBC) obtained from the mammalian subject prior to administration of an emetogenic chemotherapeutic drug, wherein assaying the biological sample comprises measuring glutathione (GSH) recycling dependent antioxidant activity of the RBC as an indicator of oxidative stress,
wherein measuring GSH recycling capacity comprises contacting the sample with hydroxyethyldisulfide (HEDS) and quantifying a concentration of β-mercaptoethanol (ME) in the sample as result of the conversion of HEDS to ME;

b. obtaining a calculation that is concentration of ME (mM) in the sample per one million total RBC, and diagnosing the subject as being predisposed to emetogenic drug-induced nausea when the calculation is ≤1.0; and   (i) administering to the subject a highly or moderately emetogenic chemotherapeutic with an antiemetic drug regimen of two or less antiemetic drugs;

(ii) administering to the subject a low emetogenic chemotherapeutic with an antiemetic drug regimen of two or less antiemetic drug;

(iii) administering to the subject a low emetogenic chemotherapeutic with no antiemetic drug;

(iv) administering to the subject a full regimen of at least 3 antiemetic drugs with an emetogenic chemotherapeutic drug;

(v) predicting delayed nausea for the subject during treatment with a highly or moderately emetogenic cytostatic chemotherapeutic drug;

(vi) predicting delayed nausea for the subject undergoing surgery requiring an emetogenic general anesthetic agent;

(vii) optimizing the subject's treatment by treating the subject with an antiemetic drug prior to, during, or after administration of said emetogenic agent; or   (viii) optimizing the subject's treatment by treating the subject with an antiemetic drug prior to, during, or after administration of a highly or moderately emetogenic chemotherapeutic drug.

2. A method for managing emetogenic drug-induced nausea in a mammalian subject with cancer, the method comprising:

a. assaying a biological sample containing RBC obtained from the mammalian subject prior to administration of an emetogenic chemotherapeutic drug,
wherein assaying the biological sample comprises GSH recycling dependent antioxidant activity of the RBC as an indicator of oxidative stress, wherein measuring GSH recycling capacity comprises contacting the sample with HEDS and quantifying a concentration of ME in the sample as result of the conversion of HEDS to ME;

b. obtaining a calculation that is concentration of ME (mM) in the sample per one million total RBC, and diagnosing the subject as being resistant to emetogenic drug-induced nausea when the calculation is >1.0; and     (i) administering to the subject a highly or moderately emetogenic chemotherapeutic with no antiemetic drug;

(ii) administering to the subject a low emetogenic chemotherapeutic with no antiemetic drug;

(iii) administering to the subject a full regimen of at least 3 antiemetic drugs with any emetogenic chemotherapeutic drug;

(iv) optimizing the subject's treatment by treating the subject with a selected antiemetic drug regimen prior to, during or after administration of a low or moderately emetogenic chemotherapeutic drug, or eliminating the antiemetic regimen; or     (v) optimizing the subject's treatment by treating the subject with an antiemetic drug regimen comprising 2 or less different antiemetic drugs prior to, during, administration of a moderately emetogenic or low emetogenic chemotherapeutic.

3. The method according to claim 1, wherein the highly emetogenic drug is cisplatin.

4. The method according to claim 1, wherein the moderately emetogenic drug is carboplatin or oxaliplatin.

5. The method according to claim 2, wherein the highly emetogenic drug is cisplatin.

6. The method according to claim 2, wherein the moderately emetogenic drug is carboplatin or oxaliplatin.

* * * * *